(12) United States Patent
Huttunen et al.

(10) Patent No.: US 12,419,578 B2
(45) Date of Patent: Sep. 23, 2025

(54) LOCKING MECHANISM FOR WEARABLE DEVICE COMPONENTS

(71) Applicant: Oura Health Oy, Oulu (FI)

(72) Inventors: Heikki Juhani Huttunen, Haukipudas (FI); Teemu Juhani Haverinen, Oulu (FI); Kari Kuisma Kanniainen, Li (FI); Antti Kalevi Lämsä, Oulu (FI); Markku Juhani Kallunki, Oulu (FI)

(73) Assignee: Oura Health Oy, Oulu (FI)

( * ) Notice: Subject to any disclaimer, the term of this patent is extended or adjusted under 35 U.S.C. 154(b) by 386 days.

(21) Appl. No.: 17/963,542

(22) Filed: Oct. 11, 2022

(65) Prior Publication Data

US 2023/0112231 A1    Apr. 13, 2023

Related U.S. Application Data

(60) Provisional application No. 63/254,653, filed on Oct. 12, 2021.

(51) Int. Cl.
*A61B 5/00* (2006.01)

(52) U.S. Cl.
CPC .......... *A61B 5/6826* (2013.01); *A61B 5/6802* (2013.01); *A61B 2562/166* (2013.01)

(58) Field of Classification Search
CPC .................... A61B 2562/166; A61B 2562/164
See application file for complete search history.

(56) References Cited

U.S. PATENT DOCUMENTS

| 2017/0042477 A1* | 2/2017 | Haverinen | A61B 5/6826 |
| 2018/0225039 A1* | 8/2018 | Warren | G06F 3/04883 |
| 2019/0086951 A1* | 3/2019 | von Badinski | G06V 40/70 |
| 2021/0177353 A1 | 6/2021 | Bhagat et al. | |
| 2024/0116202 A1 | 4/2024 | Maria et al. | |

FOREIGN PATENT DOCUMENTS

| CN | 108143427 A | 6/2018 |
| CN | 110840463 A | 2/2020 |
| CN | 214104414 U | 9/2021 |
| KR | 102038286 B1 | 10/2019 |

OTHER PUBLICATIONS

PolyCase, 3 Ways to Mount PCBs in Enclosures, Jul. 9, 2020, https://www.polycase.com/techtalk/pcb-screws/how-to-mount-pcb-in-enclosure.html, viewed on Feb. 7, 2025 (Year: 2020).*
International Search Report and Written Opinion—PCT/US2022046473—ISA/EPO—Jan. 27, 2023.

* cited by examiner

*Primary Examiner* — James M Kish
*Assistant Examiner* — James Moss
(74) *Attorney, Agent, or Firm* — Holland & Hart LLP

(57) ABSTRACT

An apparatus for a wearable device including a locking mechanism for components of the wearable device is described. A wearable ring device may include a ring-shaped housing configured to house one or more sensors configured to acquire physiological data from a user, and a flexible printed circuit board (PCB) including electrical circuitry for the one or more sensors. The wearable ring device may include one or more locking grooves disposed within an interior surface of the ring-shaped housing, the one or more locking grooves configured to receive the flexible PCB and maintain a gap between an inner circumferential surface of the ring-shaped housing and a first surface of the flexible PCB.

17 Claims, 6 Drawing Sheets

LOCKING MECHANISM FOR WEARABLE DEVICE COMPONENTS

CROSS REFERENCE

The present Application for Patent claims the benefit of U.S. Provisional Patent Application No. 63/254,653 by HUTTUNEN et al., entitled "LOCKING MECHANISM FOR WEARABLE DEVICE COMPONENTS," filed Oct. 12, 2021, assigned to the assignee hereof, and expressly incorporated by reference herein.

FIELD OF TECHNOLOGY

The following relates to wearable devices and data processing, including a locking mechanism for wearable device components.

BACKGROUND

Some wearable devices may be configured to collect physiological data from users, including temperature data, heart rate data, and the like. Many users have a desire for more insight regarding their physical health. However, a user's movement may displace or damage components of some wearable devices.

DETAILED DESCRIPTION

Figure 1:
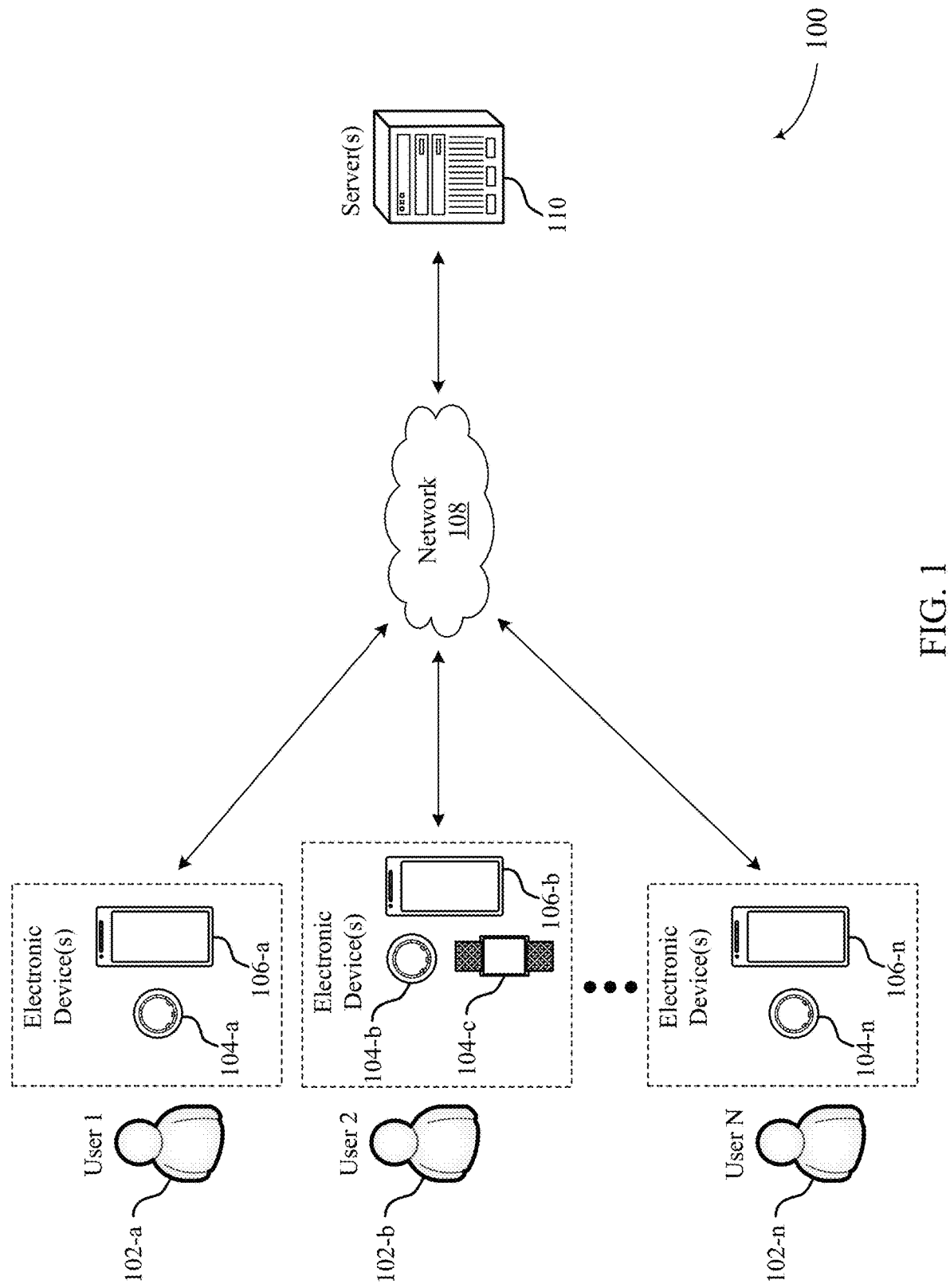
FIG. 1 illustrates an example of a system that supports a locking mechanism for wearable device components in accordance with aspects of the present disclosure.

Some wearable devices may be configured to collect data from users associated with movement and other activities. For example, some wearable devices may be configured to continuously acquire physiological data associated with a user including temperature data, heart rate data, and the like. As such, some wearable devices may be configured to house one or more sensors configured to acquire physiological data from a user. In some cases, wearable device may include a printed circuit board (PCB) including electrical circuitry for the one or more sensors.

In some cases, the PCB may be mounted or otherwise coupled with the housing of the wearable device. For example, in some implementations, the PCB may be mounted on, or may otherwise be positioned against, other components of the wearable device. As such, the PCB may bump and rub against other components, and may experience tension while the user wears the device, thereby decreasing the efficiency and accuracy of the electrical circuitry within the PCB. Moreover, a user's movement may displace or damage components (e.g., PCB) of some wearable devices, which may detrimentally affect the ability of the wearable device to efficiently and accurately acquire physiological data. Further, conventional techniques for securing the PCB within some wearable devices may result in vibration between the PCB and other components of the wearable device, which may result in a build-up of static electricity that may detrimentally affect components (e.g., sensors, memory) of the wearable device As such, conventional techniques for PCB placement within the device are deficient for multiple reasons.

Accordingly, to facilitate improved health monitoring, aspects of the present disclosure are directed to a locking mechanism for wearable device components. For example, the wearable device may include one or more locking grooves disposed within an interior surface of a housing of the wearable device, such as a ring-shaped housing of a wearable ring device. The one or more locking grooves may be configured to receive a PCB of the wireless device, such as a flexible PCB, and maintain the PCB in a defined position. For example, in the context of a wearable ring device, the locking grooves may be configured to maintain a gap between an inner circumferential surface of the ring-shaped housing and a first surface of the flexible PCB. In such cases, the gap between the housing and the PCB may help protect the PCB from being displaced or damaged.

In some implementations, the housing of the wearable device may include locking grooves for the PCB to slide into in order to lock the PCB into place within the housing. The locking grooves may position (e.g., lock) the PCB into a defined position such that a gap may exist between the PCB and the housing. The locking grooves may keep the PCB at a defined location and/or depth within the device such that the locking grooves ensure that the PCB is at the same position and/or height within the housing. For example, the PCB position inside the housing may be managed by a location of the locking grooves within the housing. In such cases, the placement of the locking grooves may ensure the presence of a gap between an inner surface of the housing and electrical circuitry of the PCB. Moreover, in the context of a wearable ring device, the locking grooves may maintain the PCB in a defined radial orientation relative to an axis of the wearable ring device.

In some implementations, the gap between the PCB and the housing of the wearable device may be filled with air or other materials to protect the PCB from damage or wear while the user wears the device. The gap and locking mechanism provided by the locking grooves within the housing may be used for alignment to lock the PCB in the housing and maintain the PCB within the wearable device. In some cases, the gap may provide shock absorption between the PCB and housing. In such cases, the accuracy and efficiency of the electrical circuitry of the PCB may increase as the tension and wear and tear on the PCB decreases. Moreover, the locking grooves and gap may prevent (or reduce) static buildup on the PCB, further protecting the PCB and associated components from damage. In some examples, the gap may be filled with an insulating material. In such cases, the insulating material may be an example of a thermal and/or electrical insulator.

Aspects of the disclosure are initially described in the context of systems supporting physiological data collection from users via wearable devices. Additional aspects of the disclosure are described in the context of example rings.

FIG. 1 illustrates an example of a system 100 that supports a locking mechanism for wearable device components in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth (e.g., Bluetooth Low Energy (BLE)), Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support an apparatus for a wearable device 104 including a locking mechanism for components of the wearable device 104. For example, a wearable ring device (e.g., wearable device 104) may include a ring-shaped housing configured to house one or more sensors configured to acquire physiological data from a user 102. The wearable ring device (e.g., wearable device 104) may include a flexible PCB including electrical circuitry for the one or more sensors. In some implementations, the wearable ring device 104 may include one or more locking grooves disposed within an interior surface of the ring-shaped housing. The one or more locking grooves may be configured to receive the flexible PCB and maintain a gap between an inner circumferential surface of the ring-shaped housing and a first surface of the flexible PCB.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
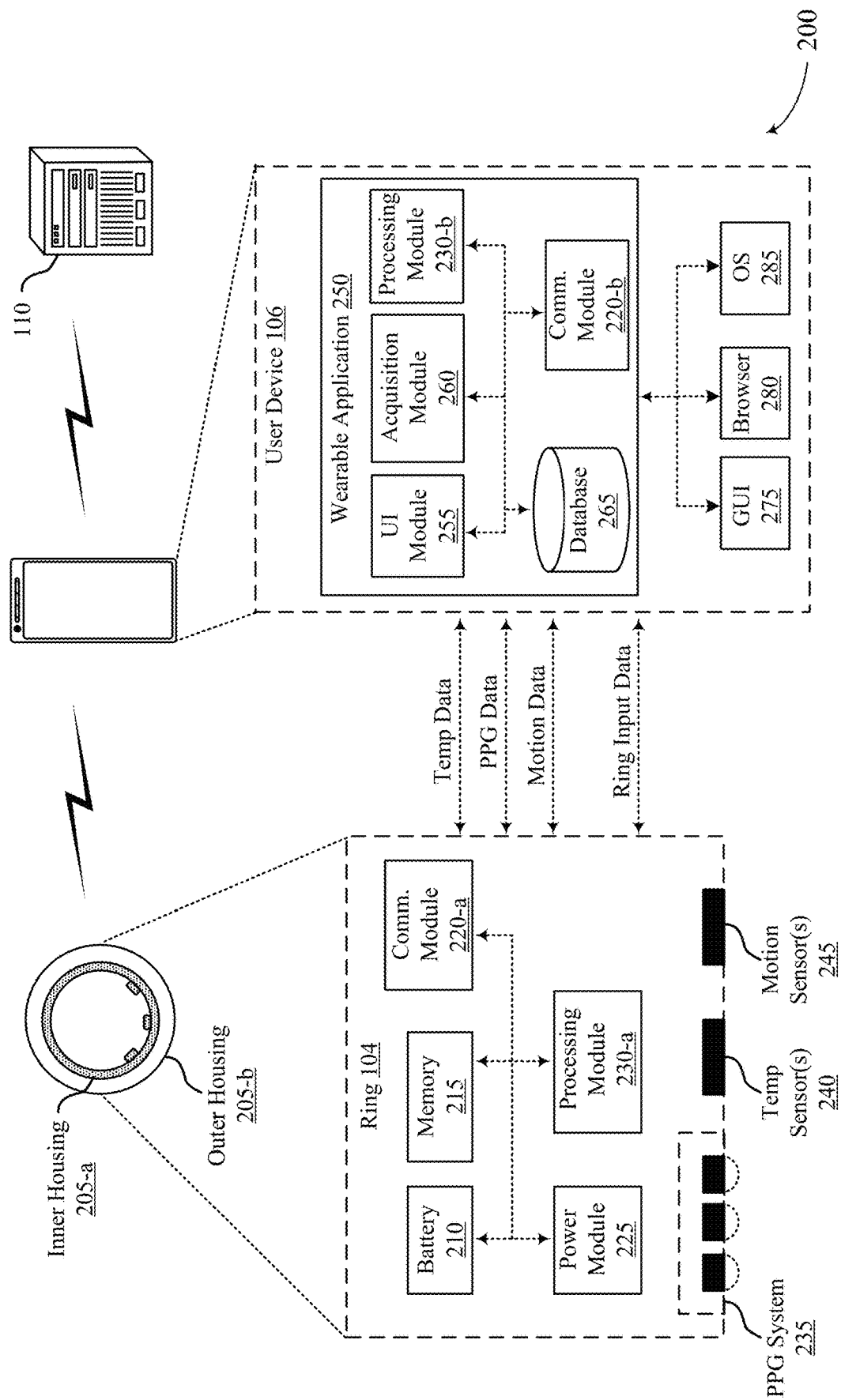
FIG. 2 illustrates an example of a system that supports a locking mechanism for wearable device components in accordance with aspects of the present disclosure.

FIG. 2 illustrates an example of a system 200 that supports a locking mechanism for wearable device components in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more PCBs, such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support an apparatus of a wearable device 104 including a locking mechanism for components of the wearable device 104. For example, a wearable ring device (e.g., wearable device 104) may include a ring-shaped housing configured to house one or more sensors configured to acquire physiological data from a user 102. The ring-shaped housing may be an example of housing 205, and the one or more sensors may be an example of temperature sensors 240, motion sensors 245, and other sensors.

The wearable ring device 104 may include a PCB (e.g., flexible PCB) including electrical circuitry for the one or more sensors. In some implementations, the wearable ring device 104 may include one or more locking grooves disposed within an interior surface of the ring-shaped housing. The one or more locking grooves may be configured to receive the flexible PCB and maintain a gap between an inner circumferential surface of the ring-shaped housing and a first surface of the flexible PCB. In some implementations, the gap may include air, a sponge material, a thermally insulating material, an electrically insulating material, a shock-absorbing material, or any combination thereof. Moreover, in some cases, the locking grooves may be configured to maintain the PCB in a defined radial orientation relative to an axis of the wearable ring device 104, and/or in a defined position/orientation relative to the inner housing 205-*a* (e.g., cover). the outer housing 205-*b,* or both.

While much of the present disclosure describes a locking mechanism in the context of a wearable ring device 104, aspects of the present disclosure may additionally or alternatively be implemented in the context of other wearable devices 104. For example, in some implementations, the locking mechanism described herein may be implemented in the context of other wearable devices 104, such as bracelets, watches, necklaces, piercings, and the like.

Figure 3:
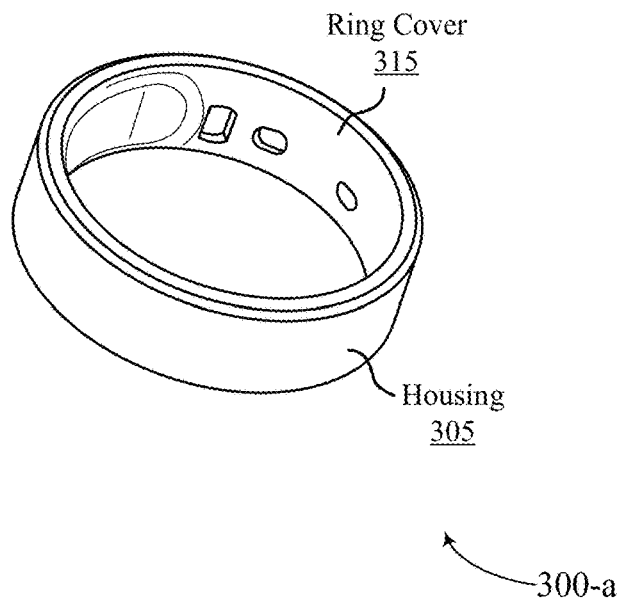
FIG. 3 illustrates examples of a ring that supports a locking mechanism for wearable device components in accordance with aspects of the present disclosure.
Figure 3:
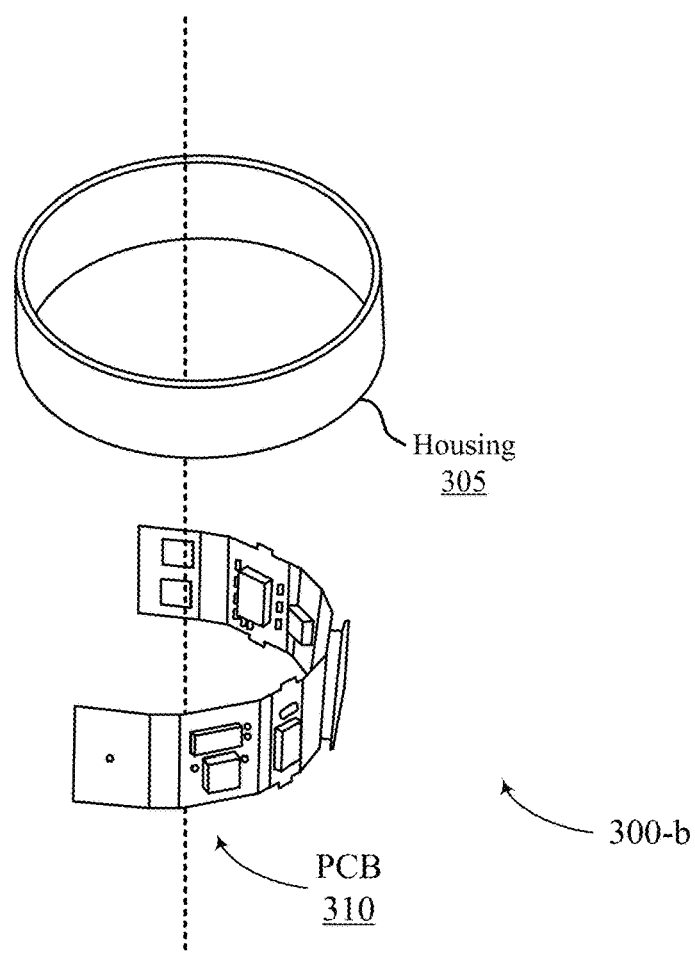

FIG. 3 illustrates examples of a wearable ring device 300 (e.g., wearable ring device 300-a, 300-b) that supports a locking mechanism for wearable device components in accordance with aspects of the present disclosure. The wearable ring device 300 may implement, or be implemented by, system 100, system 200, or both. In particular, the wearable ring device 300 may include a housing 305 as described with reference to FIG. 2. The wearable ring device 300 may also include PCB 310 and ring cover 315 (e.g., inner housing).

The housing 305 may include an outer housing for the wearable ring device 300. For example, the housing 305 may include an example of the outer housing 205-b shown and described in FIG. 2. In some aspects, the housing 305 of the wearable ring device 300 may store or otherwise include various components of the wearable ring device 300 including, but not limited to, device electronics, a power source, PCB 310, and the like that interconnect the device electronics and/or power source, and the like. In some cases, the housing 305 may be an example of a ring-shaped housing 305 configured to house one or more sensors configured to acquire physiological data from a user. In some cases, the housing 305 may extend 360° around the wearable ring device 300 relative to an axis of the wearable ring device 300. The housing 305 may be an example of a titanium material or other metal material.

The PCB 310 may include electrical circuitry for the one or more sensors. The PCB 310 may include a flexible material such that the PCB 310 may extend around a portion of the wearable ring device 300 or may extend around the entire circumference of the wearable ring device 300. For example, the PCB 310 may be ring-shaped. In some cases, the PCB 310 may extend 360° around the housing 305 relative to an axis of the housing 305. The housing 305 may store the PCB 310 and be configured to interface with the PCB 310.

The ring cover 315 may be an example of a ring-shaped cover configured to interface with the housing 305. The ring cover 315 may include an inner housing of the wearable ring device 300. For example, the ring cover 315 may include an example of the inner housing 205-a shown and described in FIG. 2. In some aspects, the ring cover 315 may store or otherwise include various components of the wearable ring device 300 including, but not limited to, device electronics, a power source, housing 305, PCB 310, and the like. The ring cover 315 may extend 360° around the housing 305 relative to an axis of the housing 305. In some cases, the ring cover 315 may include an epoxy material, a metal material, a plastic material, and the like. For example, the ring cover 315 may include an epoxy material that is vacuum molded to the housing 305. As such, the ring cover 315 and the housing 305 may be configured to store and protect the various components of the wearable ring device 300.

In some implementations, as shown in FIG. 3, the ring cover 315 may include one or more apertures or windows. In some aspects, the apertures may enable light to pass through the ring cover 315 to the components (e.g., sensors) of the PCB 310 to facilitate physiological data measurement. For example, in some cases, the ring cover 315 may include a metal material, where the apertures are filled with a transparent epoxy material that enables light to pass through the ring cover 315.

In some implementations, as will be described in further detail herein, the locking mechanism described herein may be configured to position the PCB 310 within the wearable ring device 300 such that components of the PCB 310 are aligned with (and/or aligned inside) the apertures of the ring cover 315 to enable physiological data measurement. In other words, the locking mechanism may be configured to maintain a distance between the components of the PCB 310 and the ring cover 315.

Figure 4:
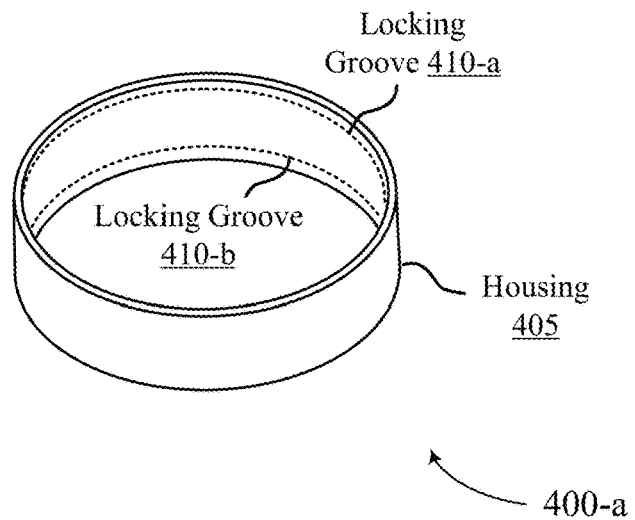
FIG. 4 illustrates examples of a ring that supports a locking mechanism for wearable device components in accordance with aspects of the present disclosure.
Figure 4:
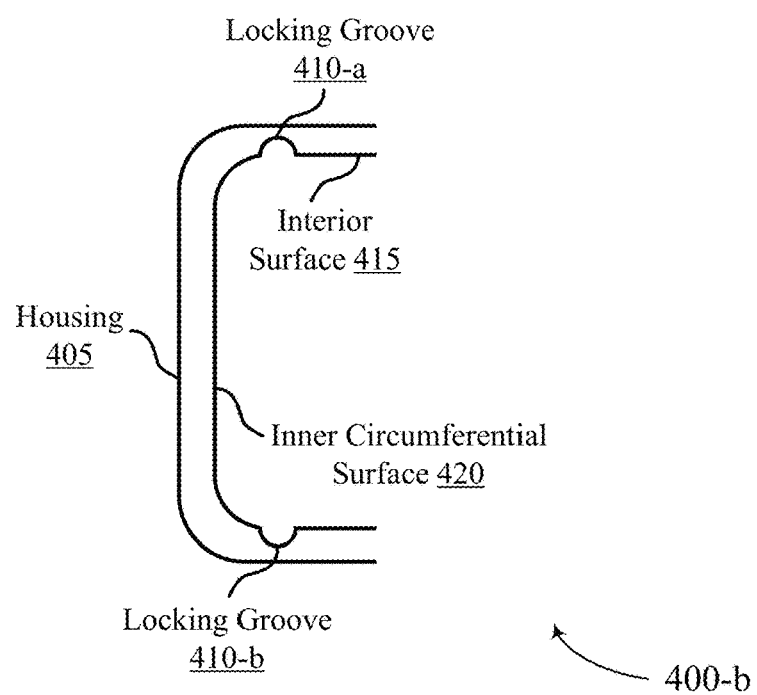

FIG. 4 illustrates examples of a wearable ring device 400 (e.g., wearable ring device 400-a, 400-b) that supports a locking mechanism for wearable device components in accordance with aspects of the present disclosure. The wearable ring device 400 may implement, or be implemented by, system 100, system 200, wearable ring device 300, or any combination thereof. In particular, the wearable ring device 400 may include a housing 405 as described with reference to FIGS. 2 and 3. The wearable ring device 400 may further include locking grooves 410. °

The wearable ring device 400-a may include the housing 405 and the locking grooves 410. For example, the locking grooves 410 may include at least a first locking groove 410-a and a second locking groove 410-b. In other examples, the locking grooves 410 may include one or more locking grooves 410. In some implementations, the locking grooves 410 may extend 360° around the housing 405 relative to an axis of the housing 405. In such cases, the locking grooves 410 may extend 360° around the wearable ring device 400-a. In other cases, the locking grooves 410 may extend only partially around the circumference of the wearable ring device 400. The first locking groove 410-a may extend parallel to the second locking groove 410-b. In such cases, the first locking groove 410-a may be positioned at the top or near a top surface of the housing 405, and the second locking groove 410-b may be positioned at the bottom or near the bottom of the housing 405. In some cases, the locking grooves 410 may be positioned between the top surface and the bottom surface of the housing 405.

The wearable ring device 400-b may illustrate a cross-sectional view of a portion of the wearable ring device 400-a. For example, the wearable ring device 400-b may include the housing 405 and the locking grooves 410-a, 410-b. The housing 405 may include an interior surface 415 and an inner circumferential surface 420. The locking grooves 410 may be disposed within an interior surface 415 of the housing 405. In some cases, the inner circumferential surface 420 may extend between the first locking groove 410-a and the second locking groove 410-b. In some implementations, the inner circumferential surface 420 of the housing 405 may include a surface of the housing that faces a user's finger when the wearable ring device 400 is being worn.

Figure 5:
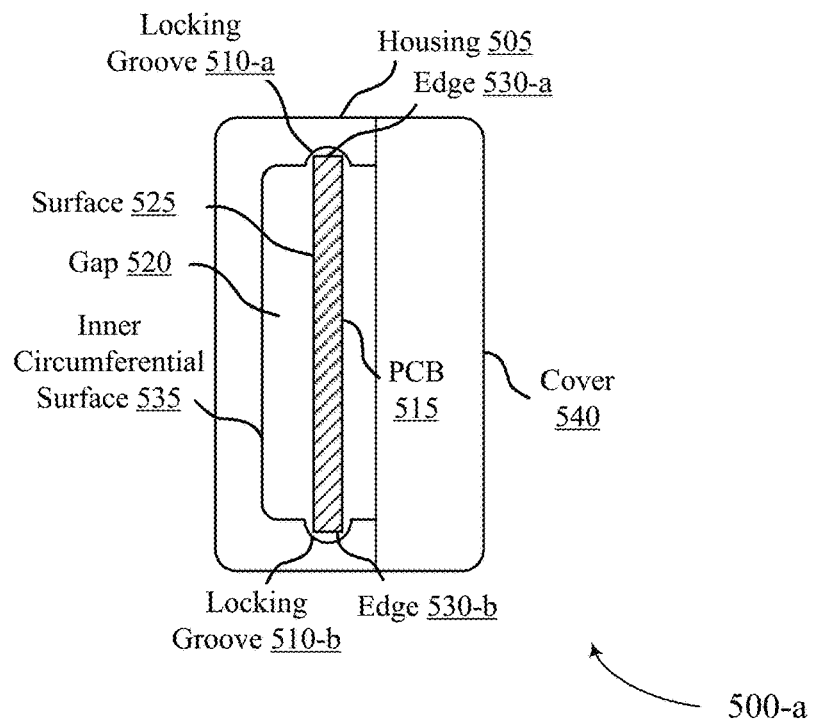
FIG. 5 illustrates examples of a cross-sectional view of a ring that supports a locking mechanism for wearable device components in accordance with aspects of the present disclosure.
Figure 5:
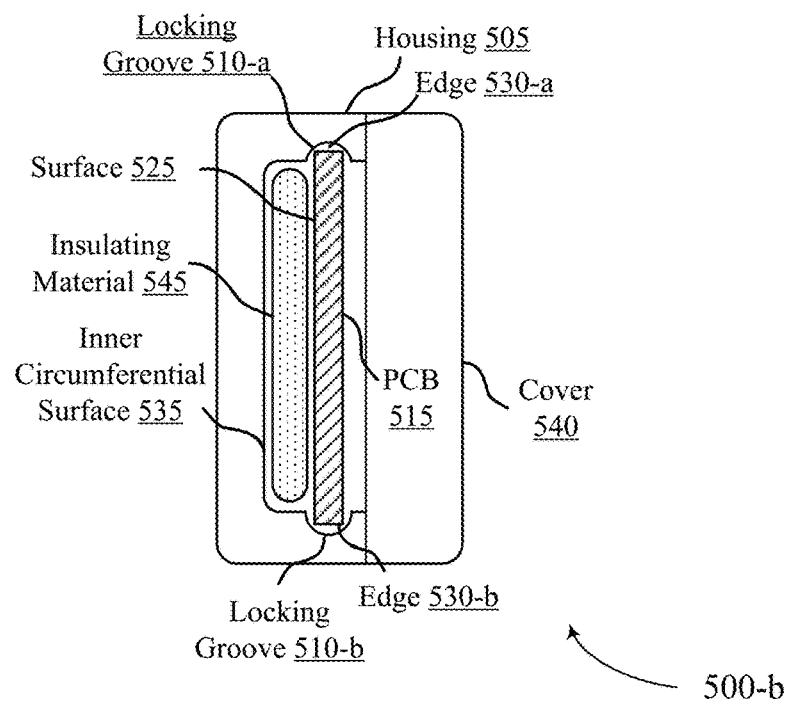

FIG. 5 illustrates examples of a cross-sectional view of a wearable ring device 500 (e.g., wearable ring device 500-a, 500-b) that supports a locking mechanism for wearable device components in accordance with aspects of the present disclosure. The wearable ring device 500 may implement, or be implemented by, system 100, system 200, wearable ring device 300, wearable ring device 400, or any combination thereof. In particular, the wearable ring device 500 may include a housing 505, locking grooves 510, PCB 515, inner circumferential surface 535, and cover 540 as described with reference to FIGS. 2 through 4.

The cross-sectional view of the wearable ring device 500-a may include a gap 520. The gap 520 may extend between the inner circumferential surface 535 and the surface 525 of the PCB 515. In such cases, the locking grooves 510-*a* and 510-*b* may be configured to receive the PCB 515 and maintain the gap 520 between the inner circumferential surface 535 of the housing 505 and the surface 525 of the PCB 515. In other words, the locking grooves 510 may be configured to maintain the PCB 515 in a defined position within the housing 505 relative to the housing 505, the cover 540, or both.

For example, the locking grooves 510 may position the PCB 515 in a correct position to ensure that there is enough distance from the top of components within the PCB 515 (e.g., components on a surface 525 of the PCB 515) to the inner circumferential surface 535 of the housing 505. The distance between the surface 525 of the PCB 515 and the inner circumferential surface 535 of the housing 505 may be determined based on the thickness of the PCB 515, the thickness of the housing 505, the circuitry of the PCB 515, or a combination thereof. In this regard, in some implementations, the locking mechanism described herein may enable the PCB 515 to have electrical circuitry and components on both sides of the PCB 515 (e.g., on a surface 525 facing the inner circumferential surface 535 of the housing 505, and on a second surface facing the cover 540).

Additionally, or alternatively, the locking grooves 510 may be configured to maintain the PCB 515 in a defined position relative to the cover 540. For example, the locking grooves 510 may be configured to maintain the PCB 515 in a defined radial position such that components of the PCB 515 (e.g., LEDs, photodetectors) align with one or more apertures within the cover 540. Moreover, the locking grooves 510 may be configured to maintain the PCB 515 in a defined position such that components of the PCB 515 extend into the apertures of the cover 540 to facilitate physiological data measurement.

In some implementations, one or more antenna elements may be disposed within the gap 520 between the inner circumferential surface 535 of the housing 505 and the PCB 515. The one or more antenna elements may be configured to wirelessly couple one or more components of the wearable ring device (e.g., wearable ring device 500-*a*) with a user device 106. In such cases, the antennas may increase a Bluetooth signal (e.g., BLE signal) or other wireless signal between the wearable ring device 500-*a* and a user device 106.

The PCB 515 may include a first edge 530-*a* and a second edge 530-*b*. The first edge 530-*a* may be configured to slidably couple with the first locking groove 510-*a*, and the second edge 530-*b* may be configured to slidably couple with the second locking groove 510-*b*. In other words, the first edge 530-*a* may be configured to slide within the first locking groove 510-*a*, and the second edge 530-*b* may be configured to slide within the second locking groove 510-*b*. The second edge 530-*b* may be opposite the first edge 530-*a*.

In some cases, the locking grooves 510 may be configured to arrange the PCB 515 in a defined radial orientation relative to an axis of the housing 505 by coupling the first locking groove 510-*a* with the first edge 530-*a* and coupling the second locking groove 510-*b* with the second edge 530-*b*. In other words, the locking grooves 510 may be configured to receive the PCB 515 such that components of the PCB 515-*a* (e.g., sensors, electrical circuitry) are correctly positioned within the wearable ring device 500 in their intended positions when the PCB 515 is inserted within the locking grooves 510 (e.g., so that sensors of the PCB 515 are radially aligned with apertures of the cover 540).

The locking grooves 510 may be configured to maintain the PCB 515 in a defined position relative to the housing 505 such that the gap 520 between the inner circumferential surface 535 of the housing 505 and the surface 525 of the PCB 515 is uniform across at least a portion of the housing 505. In such cases, the gap 520 between the housing 505 and the PCB 515 may be uniform. For example, a distance between the inner circumferential surface 535 and the surface 525 of the PCB 515 may be the same across a portion of the housing 505.

In some implementations, the gap 520 between the PCB 515 and the housing 505 may be filled with a material other than air. For example, as shown in the cross-sectional view of the wearable ring device 500-*b*, the wearable ring device 500-*b* may include an insulating material 545. In some cases, the insulating material 545 may be disposed within the gap 520 between the inner circumferential surface 535 of the housing 505 and the PCB 515. In such cases, the locking grooves 510-*c* and 510-*d* may be configured to receive the PCB 515 and maintain the insulating material 545 between the inner circumferential surface 535 of the housing 505 and the surface 525 of the PCB 515. In some aspects, the insulating material 545 may be configured to provide improved protection for the PCB 515. In this regard, the insulating material 545 may include a sponge material, a thermally insulating material, an electrically insulating material, a shock-absorbing material, or any combination thereof.

In some aspects, the wearable ring device 500 (e.g., wearable ring device 500-*a*, wearable ring device 500-*b*) may include a cover 540 that is configured to interface with (e.g., couple to) the housing 505. In some aspects, the cover 540 may be configured to couple with the housing 505 in order to contain and protect the various components of the wearable ring device 500 (e.g., PCB 515). In some aspects, the cover 540 may include an epoxy material, a metal material, a plastic material, or any combination thereof. In the context of an epoxy material, the epoxy material of the cover 540 may be molded in a vacuum (e.g., vacuum molded). In such cases, the epoxy material of the cover 540 may fill a portion of the ring that extends between the cover 540 and the PCB 515. In other words, in some implementations, the cover 540 may be molded to the wearable ring device 500 such that the cover 540 is in physical contact with a surface of the PCB 515 opposite the surface 525. Additionally, or alternatively, the epoxy material of the cover 540 may be coupled to the housing 505 such that the epoxy material of the cover 540 fills at least a portion of the gap 520 between the PCB 515 and the inner circumferential surface 535 of the housing 505.

As described previously herein, according to some conventional techniques, the PCB of a wearable device may be attached to (or against) other components of the wearable device to lock the PCB in place. However, such techniques may result in the PCB rubbing or vibrating against other components, which may result in damage and/or static electricity buildup (which may detrimentally affect components of the PCB). Comparatively, the locking mechanism described herein, including the locking grooves 510, may enable the PCB 515 to be secured in place within the wearable ring device 500 without the PCB 515 resting or rubbing against other components, thereby protecting the PCB 515 from damage and static electricity buildup.

Figure 6:
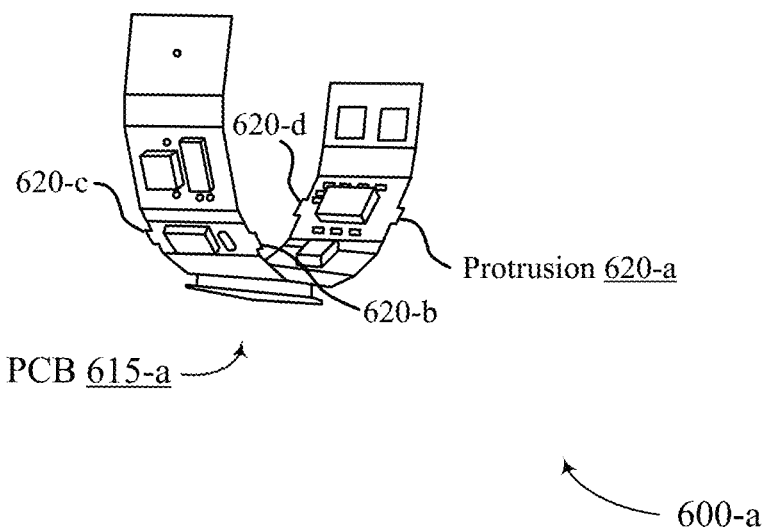
FIG. 6 illustrates examples of a portion of a ring that supports a locking mechanism for wearable device components in accordance with aspects of the present disclosure.
Figure 6:
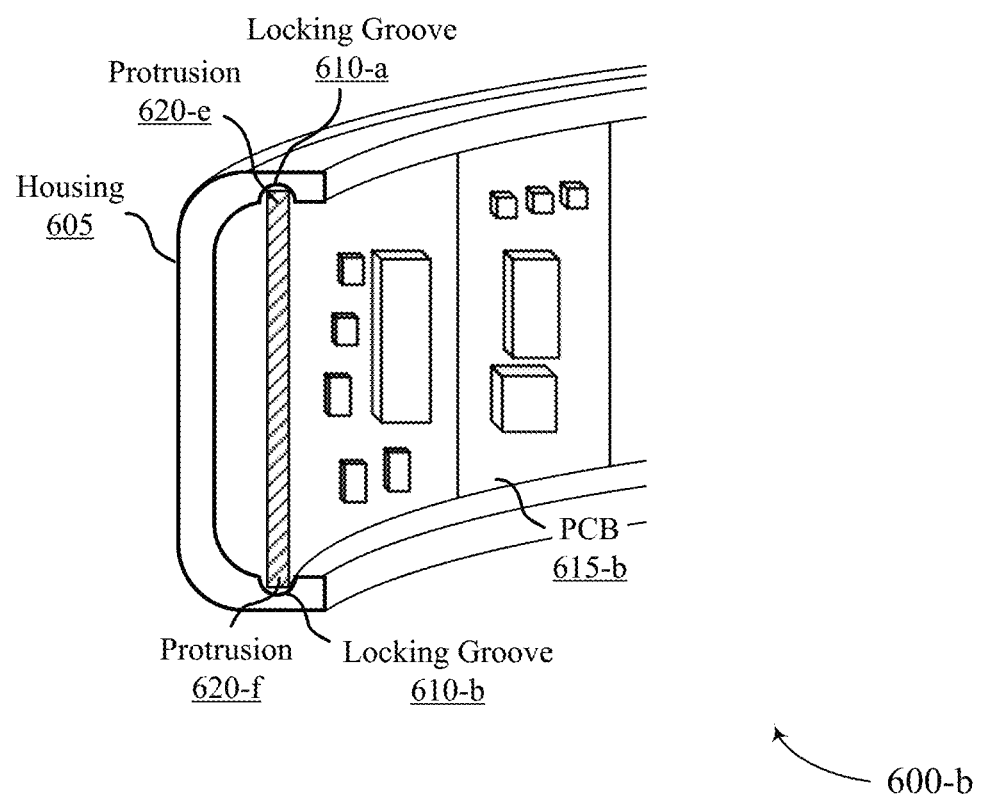

FIG. 6 illustrates examples of a portion of a wearable ring device 600 (e.g., wearable ring device 600-*a*, 600-*b*) that supports a locking mechanism for wearable device components in accordance with aspects of the present disclosure. The wearable ring device 600 may implement, or be implemented by, system 100, system 200, wearable ring devices 300-500, or any combination thereof. In particular, the wearable ring device 600 may include a housing 605, locking grooves 610, and PCB 615 as described with reference to FIGS. 2 through 5. The wearable ring device 600 may further include protrusions 620.

The portion of the wearable ring device 600-*a* may be an example of the PCB 615-*a* (e.g., flexible PCB 615-*a*) that may be housed within housing 605. The PCB 615-*a* may include a plurality of protrusions 620. The protrusions 620 may extend from the PCB 615. For example, the PCB 615-*a* may include at least a first protrusion 620-*a* and a second protrusion 620-*b* positioned at or near a first surface/edge of the PCB 615-*a* (e.g., along a top edge of the PCB 615-*a*).

The PCB 615-*a* may also include one or more protrusions 620 (e.g., protrusions 620-*c,* 620-*d*) positioned at or near a second surface/edge of the PCB 615-*a* (e.g., along a bottom edge of the PCB 615-*a*). In such cases, the top protrusions 620 (e.g., protrusion 620-*a,* 620-*b*) may be positioned opposite of the bottom protrusions 620 (e.g., protrusions 620-*c,* 620-*d*). In some cases, the protrusions 620 may be positioned 360° around the PCB 615-*a* relative to an axis of the PCB 615-*a*. In some cases, the PCB 615-*a* may include protrusions 620 that are positioned at regular or irregular intervals across at least a portion of the PCB 615-*a*.

The portion of the wearable ring device 600-*b* may include the housing 605, the locking groove 610, the PCB 615-*b*, and protrusions 620-*e,* 620-*f* The protrusions 620-*e,* 620-*f* may be configured to interface with the locking grooves 610-*a,* 610-*b* to maintain the PCB 615-*b* within a defined position within the housing 605. In such cases, the PCB 615-*b* may include locking features (e.g., protrusions 620-*e,* 620-*f*) that may interface with the locking groove 610-*a,* 610-*b*.

The protrusions 620 may provide increased flexibility in the PCB 615. For example, the protrusions 620 may include a flexible or electrically insulating material (e.g., rubber, epoxy, etc.) such that the tension is retained within the protrusions 620 without transferring the tension to the central structure of the PCB 615 (e.g., including rigid circuitry). In such cases, the protrusions 620 may interface with the locking grooves 610 to reduce a surface area of the PCB 615 that is in physical contact with the locking grooves 610/housing 605. In other words, in cases where the protrusions 620 are positioned along top and bottom edges of the PCB 615, the protrusions 620 may interface with the locking grooves 610 such that the other portions of the top and bottom edges are not positioned within the locking grooves 610 when the protrusions are inserted within the locking grooves 610. By minimizing or reducing contact between the PCB 615-*b* and the other components of the wearable ring device 600, such as the housing 605, techniques described herein may reduce friction between the PCB 615-*b* and other components, thereby reducing wear and tear, and reducing or eliminating static electricity buildup within the wearable device 104.

It should be noted that the methods described above describe possible implementations, and that the operations and the steps may be rearranged or otherwise modified and that other implementations are possible. Furthermore, aspects from two or more of the methods may be combined.

An apparatus is described. The apparatus may include a ring-shaped housing configured to house one or more sensors configured to acquire physiological data from a user, a flexible PCB comprising electrical circuitry for the one or more sensors, and one or more locking grooves disposed within an interior surface of the ring-shaped housing, the one or more locking grooves configured to receive the flexible PCB and maintain a gap between an inner circumferential surface of the ring-shaped housing and a first surface of the flexible PCB.

In some examples of the apparatus, the apparatus includes an insulating material disposed within the gap between the inner circumferential surface of the ring-shaped housing and the flexible PCB.

In some examples of the apparatus, the insulating material comprises a sponge material, a thermally insulating material, an electrically insulating material, a shock-absorbing material, or any combination thereof In some examples of the apparatus, the apparatus includes one or more antenna elements disposed within the gap between the inner circumferential surface of the ring-shaped housing and the flexible PCB, wherein the one or more antenna elements are configured to wirelessly couple one or more components of the wearable ring device with a user device.

In some examples of the apparatus, the flexible PCB includes a plurality of protrusions extending from the flexible PCB, wherein the plurality of protrusions are configured to interface with the one or more locking grooves to maintain the flexible PCB within a defined position within the ring-shaped housing.

In some examples of the apparatus, the one or more locking grooves comprise a first locking groove and a second locking groove. In some examples, the flexible PCB comprises a first edge configured to slidingly couple with the first locking groove, and a second edge opposite the first edge, the second edge configured to slidingly couple with the second locking groove.

In some examples of the apparatus, the apparatus includes a ring-shaped cover configured to interface with the ring-shaped housing, wherein the ring-shaped cover comprises an epoxy material.

In some examples of the apparatus, the one or more locking grooves are configured to arrange the flexible PCB in a defined radial orientation relative to an axis of the ring-shaped housing.

In some examples of the apparatus, the one or more locking grooves extend 360° around the ring-shaped housing relative to an axis of the ring-shaped housing.

In some examples of the apparatus, the one or more locking grooves are configured to maintain the flexible PCB in a defined position relative to the ring-shaped housing such that the gap between the inner circumferential surface of the ring-shaped housing and the first surface of the flexible PCB is uniform across at least a portion of the ring-shaped housing.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device comprising:
   a housing configured to house one or more sensors configured to acquire physiological data from a user, the housing comprising:
      an outer housing; and
      an inner cover coupled with the outer housing, the inner cover comprising one or more apertures, wherein the one or more sensors are disposed at least partially between the outer housing and the inner cover;
   a flexible printed circuit board comprising electrical circuitry for the one or more sensors; and
   one or more locking grooves disposed within an interior surface of the outer housing, the one or more locking grooves configured to receive the flexible printed circuit board and maintain a gap between an inner circumferential surface of the outer housing and a first surface of the flexible printed circuit board, and wherein the one or more locking grooves extend around only a portion of a circumference of the outer housing and are configured to position the flexible printed circuit board in a defined radial orientation relative to an axis of the wearable ring device such that the one or more sensors are aligned with the one or more apertures of the inner cover.

2. The wearable ring device of claim 1, further comprising:
   an insulating material disposed within the gap between the inner circumferential surface of the outer housing and the first surface of the flexible printed circuit board.

3. The wearable ring device of claim 2, wherein the insulating material comprises a sponge material, a thermally insulating material, an electrically insulating material, a shock-absorbing material, or any combination thereof.

4. The wearable ring device of claim 2, further comprising:
   one or more antenna elements disposed within the gap between the inner circumferential surface of the outer housing and the first surface of the flexible printed circuit board, wherein the one or more antenna elements are configured to wirelessly couple one or more components of the wearable ring device with a user device.

5. The wearable ring device of claim 1, wherein the flexible printed circuit board comprises:
a plurality of protrusions extending from the flexible printed circuit board, wherein the plurality of protrusions are configured to interface with the one or more locking grooves to maintain the flexible printed circuit board in the defined radial orientation within the housing.

6. The wearable ring device of claim 1, wherein the one or more locking grooves comprise a first locking groove and a second locking groove, and wherein the flexible printed circuit board comprises:
a first edge configured to slidingly couple with the first locking groove; and
a second edge opposite the first edge, the second edge configured to slidingly couple with the second locking groove.

7. The wearable ring device of claim 1,
wherein the inner cover comprises a metal material, a plastic material, or both, wherein the one or more apertures are disposed within the metal material, the plastic material, or both.

8. The wearable ring device of claim 1, wherein the one or more locking grooves are configured to arrange the flexible printed circuit board in the defined radial orientation such that the one or more sensors are radially aligned with the one or more apertures of the inner cover relative to the axis of the outer housing.

9. The wearable ring device of claim 1, wherein the flexible printed circuit board extends around the portion of the circumference of the outer housing.

10. The wearable ring device of claim 1, wherein the one or more locking grooves are configured to maintain the flexible printed circuit board in a defined position relative to the inner circumferential surface of the outer housing such that the gap between the inner circumferential surface of the outer housing and the first surface of the flexible printed circuit board is uniform across at least a portion of the outer housing.

11. The wearable ring device of claim 1, wherein the flexible printed circuit board comprises a plurality of protrusions extending from the flexible printed circuit board that are configured to interface with the one or more locking grooves, and wherein the plurality of protrusions comprise a flexible and electrically-insulating material that is configured to reduce or eliminate static electricity buildup within the wearable ring device.

12. The wearable ring device of claim 11, wherein the flexible and electrically-insulating material comprises rubber or epoxy.

13. The wearable ring device of claim 1, wherein the one or more sensors are disposed on a second surface of the flexible printed circuit board opposite the first surface, wherein the flexible printed circuit board comprises one or more additional components disposed on the first surface of the flexible printed circuit board, and wherein a height of the gap between the inner circumferential surface of the outer housing and the first surface of the flexible printed circuit board is based at least in part on a height of the one or more additional components.

14. The wearable ring device of claim 1, wherein the one or more locking grooves comprise a first locking groove and a second locking groove disposed within the interior surface of the outer housing, wherein a first edge and a second edge of the flexible printed circuit board are configured to be inserted into the first locking groove and the second locking groove, respectively, to maintain the flexible printed circuit board in the defined radial orientation.

15. The wearable ring device of claim 1, wherein the one or more locking grooves are configured to arrange the flexible printed circuit board in the defined radial orientation such that the one or more sensors are radially aligned with and extend into the one or more apertures of the inner cover.

16. The wearable ring device of claim 1,
wherein the one or more sensors are disposed on a second surface of the flexible printed circuit board opposite the first surface, wherein the flexible printed circuit board comprises one or more additional components disposed on the first surface of the flexible printed circuit board,
wherein the one or more locking grooves are configured to maintain the flexible printed circuit board within a defined position between the outer housing and the inner cover such that the gap between the inner circumferential surface of the outer housing and the first surface of the flexible printed circuit board is greater than a height of the one or more additional components, and such that the one or more sensors extend into the one or more apertures of the inner cover.

17. The wearable ring device of claim 1, wherein the one or more apertures are filled with a transparent epoxy material that is configured to enable light emitted by the one or more sensors to pass through the inner cover.

* * * * *